US 7,084,868 B2

(12) United States Patent
Farag et al.

(10) Patent No.: US 7,084,868 B2
(45) Date of Patent: Aug. 1, 2006

(54) SYSTEM AND METHOD FOR 3-D DIGITAL RECONSTRUCTION OF AN ORAL CAVITY FROM A SEQUENCE OF 2-D IMAGES

(75) Inventors: Aly A. Farag, Louisville, KY (US); David Tasman, Louisville, KY (US); Sameh M. Yamany, Weston, FL (US)

(73) Assignee: University of Louisville Research Foundation, Inc., Louisville, KY (US)

(*) Notice: Subject to any disclaimer, the term of this patent is extended or adjusted under 35 U.S.C. 154(b) by 821 days.

(21) Appl. No.: 09/842,587

(22) Filed: Apr. 26, 2001

(65) Prior Publication Data

US 2002/0028418 A1 Mar. 7, 2002

Related U.S. Application Data

(60) Provisional application No. 60/199,913, filed on Apr. 26, 2000.

(51) Int. Cl.
*G06T 17/00* (2006.01)

(52) U.S. Cl. .................................................. 345/419
(58) Field of Classification Search ................ 345/418, 345/419, 420, 423, 424, 428, 581
See application file for complete search history.

(56) References Cited

U.S. PATENT DOCUMENTS 6,192,329 B1 * 2/2001 Rider et al. ..................... 703/6
6,414,708 B1 * 7/2002 Carmeli et al. ................ 348/42

OTHER PUBLICATIONS

Ahmed, A., et al., "3D Reconstruction of the Human Jaw from a Sequence of Images", *Proceedings of the IEEE Computer Vision and Pattern Recognition Conference (CVPR)*, Puerto Rico, pp. 646–653, (Jun. 1997).

Ahmed, M.T., et al., "Neurocalibration: A Neural Network that can Tell Camera Calibration Parameters", *Proceedings of the IEEE International Conference on Computer Vision (ICCV)*, Greece, pp. 463–468, (Sep. 1999).

Besl, P.J., et al., "A Method for Registration of 3-D Shapes", *IEEE Transactions on Pattern Analysis and Machine Intelligence*, 14 (2), pp. 239–256, (Feb. 1992).

Goshtasby, A.A., et al., "A System for Digital Reconstruction of Gypsum Dental Casts", *IEEE Transactions on Medical Imaging*, 16 (5), pp. 664–674, (Oct. 1997).

Mostafa, M.G., et al., "Integrating Shape from Shading and Range Data Using Neural Network", *Proceedings of the IEEE Computer Vision and Pattern Recogniation Conference (CVPR)*, Fort Collins, Colorado, USA, pp. 15–20, (Jun. 1999).

Wei, G., et al., "Learning Shape from Shading by a Multilayer Network", *IEEE Transactions on Neural Networks*, 7 (4), pp. 985–995, (Jul. 1996).

(Continued)

*Primary Examiner*—Mark Zimmerman
*Assistant Examiner*—Cliff N. Vo
(74) *Attorney, Agent, or Firm*—Viksnins Harris & Padys PLLP

(57) ABSTRACT

Systems and methods are provided through which a model-based vision system for dentistry which assists in diagnosis, treatment planning and surgical simulation. The present invention includes an integrated computer vision system that constructs a three-dimensional (3-D) model of the patient's dental occlusion using an intra-oral video camera. A modified shape from shading technique, using perspective projection and camera calibration, extracts the 3-D information from a sequence of two-dimensional images of the jaw. Data fusion of range data and 3-D registration techniques develop a complete 3-D digital jaw model. Triangulation of the 3-D digital model is then performed, and optionally, a solid 3-D model is reconstructed.

29 Claims, 8 Drawing Sheets

OTHER PUBLICATIONS

Yamany, S.M., et al., "A 3–D reconstruction System for Human Jaw Using a Sequence of Optical Images", *IEEE Transactions on Medical Imaging,* 19 (*5*), pp. 538–547, (May 2000).

Yamany, S.M., et al., "A New Genetic–Based Technique for Matching 3–D Curves and Surfaces", *Pattern Recognition* 32 (*10*), p. 1817, (1999).

Yamany, S.M., et al., "A Robust 3–D Reconstruction System for Human Jaw Modeling", *Proceedings of the 2nd International Conference on Medical Image Computing and Computer–Assisted Intervention (MICCAI '99),* Cambridge, England, pp. 778–787, (Sep. 1999).

Yamany, S.M., et al., "A System for Human Jaw Modeling Using Intra–Oral Images", *Proceedings of the IEEE Engineering in Medicine and Biology Society (EMBS) Conference,* Hong Kong, pp. 563–566, (Oct. 1998).

Yamany, S.M., et al., "Free–Form Object Recognition and Registration Using Surface Signatures", *Proceedings of the IEEE International Conference on Computer Vision (ICCV),* Greece, pp. 1098–1104, (Sep. 1999).

Yamany, S.M., et al., "Orthodontics Measurements using Computer Vision", *Proceedings IEEE Engineering in Medicine and Biology Society (EMBS) Conference,* Hong Kong, pp. 534–539, (Oct. 1998).

* cited by examiner

SYSTEM AND METHOD FOR 3-D DIGITAL RECONSTRUCTION OF AN ORAL CAVITY FROM A SEQUENCE OF 2-D IMAGES

RELATED APPLICATION

This application claims the benefit of U.S. Provisional Application Ser. No. 60/199,913, filed Apr. 26, 2000 under 35 U.S.C. 119(e).

FIELD OF THE INVENTION

This invention relates generally to digital dental imaging, and more particularly to three-dimensional dental imaging.

BACKGROUND OF THE INVENTION

Dentistry requires accurate 3-D representation of the teeth and jaw for diagnostic and treatment purposes. For example, orthodontic treatment involves the application, over time, of force systems to teeth to correct malocclusion. In order to evaluate tooth movement progress, the orthodontist monitors this movement by means of visual inspection, intra-oral measurements, fabrication of casts, photographs, and radiographs; this process is both costly and time consuming. Moreover, repeated acquisition of radiographs may result in untoward effects. Obtaining a cast of the jaw is a complex operation for the dentist, an unpleasant experience for the patient, and also may not provide all the necessary details of the jaw.

Oral and maxillofacial radiology provides the dentist with abundant 3-D information of the jaw. Current and evolving methods include computed tomography (CT), tomosynthesis, tuned-aperture CT (TACT), and localized, or "cone-beam," computed tomography. While oral and maxillofacial radiology is now widely accepted as a routine technique for dental examinations, the equipment is rather expensive and the resolution is frequently too low for 3-D modeling of dental structures. Furthermore, the radiation dose required to enhance both contrast and spatial resolution can be unacceptably high.

Much effort has been focused recently on computerized diagnosis in dentistry. One solution is an expert system where cephalometric measurements are acquired manually from the analysis of radiographs and plaster models. Another solution provides a computer-vision technique for the acquisition of jaw data from inexpensive dental wafers, which is capable of obtaining imprints of the teeth. Conventional 3-D systems for dental applications commonly rely on obtaining an intermediate solid model of the jaw (cast or teeth imprints) and then capturing the 3-D information from that model. User interaction is needed in such systems to determine the 3-D coordinates of fiducial reference points on a dental cast. Other systems that measure the 3-D coordinates have been developed using either mechanical contact or a traveling light principle. Yet another conventional solution includes a range scanner based on white light to reconstruct the cast. The scanner used the subtractive light principle to create very thin shadow profiles on the cast.

For the reasons stated above, and for other reasons stated below which will become apparent to those skilled in the art upon reading and understanding the present specification, there is a general need to replace conventional approaches in diagnosis, treatment planning, surgical simulation and prosthetic replacements. More specifically, there is a need in the art for three-dimensional (3-D) dental imagery not using expensive, low-resolution and potentially harmful radiography, intermediate physical casts. There is also a need for fabricating dental casts in a manner that does not require time consuming and non-renewable direct application of material to the dental surfaces. Moreover, there is a need for a data acquisition system that obtains sequences of calibrated video images, with respect to a common reference in 3-D space, of the upper and/or lower jaw using an intraoral cavity camera. There is also a need for methods of accurate 3-D reconstruction of the upper and/or lower jaw from the acquired sequence of intraoral cavity images. There is a further need for a shape-from-shading process that incorporates the parameters of the intraoral cavity camera. There is yet another need for a robust process for the fusion of data acquired from multiple views of the intraoral cavity camera. There is still another need for the implementation of a fast an accurate 3-D registration. There is still yet another need for specific object segmentation and recognition of individual tooth information for further analysis and simulations. There is still yet a further need to enable study and simulation of tooth movement based on finite element and deformable model methods.

SUMMARY OF THE INVENTION

The above-mentioned shortcomings, disadvantages and problems are addressed by the present invention, which will be understood by reading and studying the following specification.

The present invention provides a system for dentistry and orthodontics to replace traditional approaches in diagnosis, treatment planning, surgical simulation, and prosthetic replacements. The present invention provides a data acquisition system that obtains sequences of calibrated video images, with respect to a common reference in three-dimensional (3-D) space, of an upper/lower jaw using a small intra-oral camera. The present invention also provides methods for 3-D reconstruction from the acquired sequence of intra-oral images. The present invention further provides an algorithm for shape from shading that incorporates camera parameters. The present invention additionally provides a process for the fusion of data acquired from multiple views, including the implementation of an accurate and fast 3-D data registration. The present invention also provides an object segmentation and recognition system to separate and recognize individual 3-D tooth information for further analysis and simulations. The present invention in addition provides methods to enable study and simulation of tooth movement based on the finite element method and deformable model approaches. In varying embodiment, the present invention is implemented in various dental practices including implants, tooth alignment, craniofacial surgery, teledentistry, dental education and training, and the analysis and simulation of dental operations including tooth alignment, implant planing, restoration, and measurement of distances and orientation of teeth with respect to each other.

In one aspect of the present invention, a method includes receiving a plurality of two-dimensional images of an oral cavity, and generating at least one three-dimensional image of the oral cavity from the plurality of two-dimensional images. In another aspect of the present invention, a computerized apparatus includes a digitizer providing five degrees of freedom, the digitizer having an arm, a charge coupled device camera, rigidly mounted on the arm of the digitizer, and a computer, operably coupled to the digitizer and the camera that receives coordinate measurements from the digitizer and a plurality of two-dimensional images from the camera and generates a digital three-dimensional model from the coordinate measurements and from the plurality of two-dimensional images.

The present invention discloses the generation of a 3-D model of the jaw, not from a cast, but from the actual human jaw. The present invention disclose systems and method of data acquisition performed directly on a jaw using a small off the shelf charge coupled device camera in which the acquisition time is relatively short and is less discomforting to the patient compared to current practices. The acquired digital model is optionally stored with the patient data and optionally retrieved on demand. The model optionally is transmitted over a communication network to different remote practitioners for further assistance in diagnosis and treatment planning. Dental measurements and virtual restoration are optionally performed and analyzed from the digital model.

The present invention describes systems, clients, servers, methods, and computer-readable media of varying scope. In addition to the aspects and advantages of the present invention described in this summary, further aspects and advantages of the invention will become apparent by reference to the drawings and by reading the detailed description that follows.

DETAILED DESCRIPTION OF THE INVENTION

In the following detailed description of embodiments of the invention, reference is made to the accompanying drawings that form a part hereof, and in which is shown by way of illustration specific embodiments in which the invention may be practiced. These embodiments are described in sufficient detail to enable those skilled in the art to practice the invention, and it is to be understood that other embodiments may be utilized and that logical, mechanical, electrical and other changes may be made without departing from the scope of the present invention. The following detailed description is, therefore, not to be taken in a limiting sense, and the scope of the present invention is defined only by the appended claims.

The detailed description is divided into five sections. In the first section, the hardware and the operating environment in conjunction with which embodiments of the invention may be practiced are described. In the second section, a system level overview of the invention is presented. In the third section, methods for an embodiment of the invention are provided. In the fourth section, a particular object-oriented Internet-based implementation of the invention is described. Finally, in the fifth section, a conclusion of the detailed description is provided.

Hardware and Operating Environment

Figure 1:
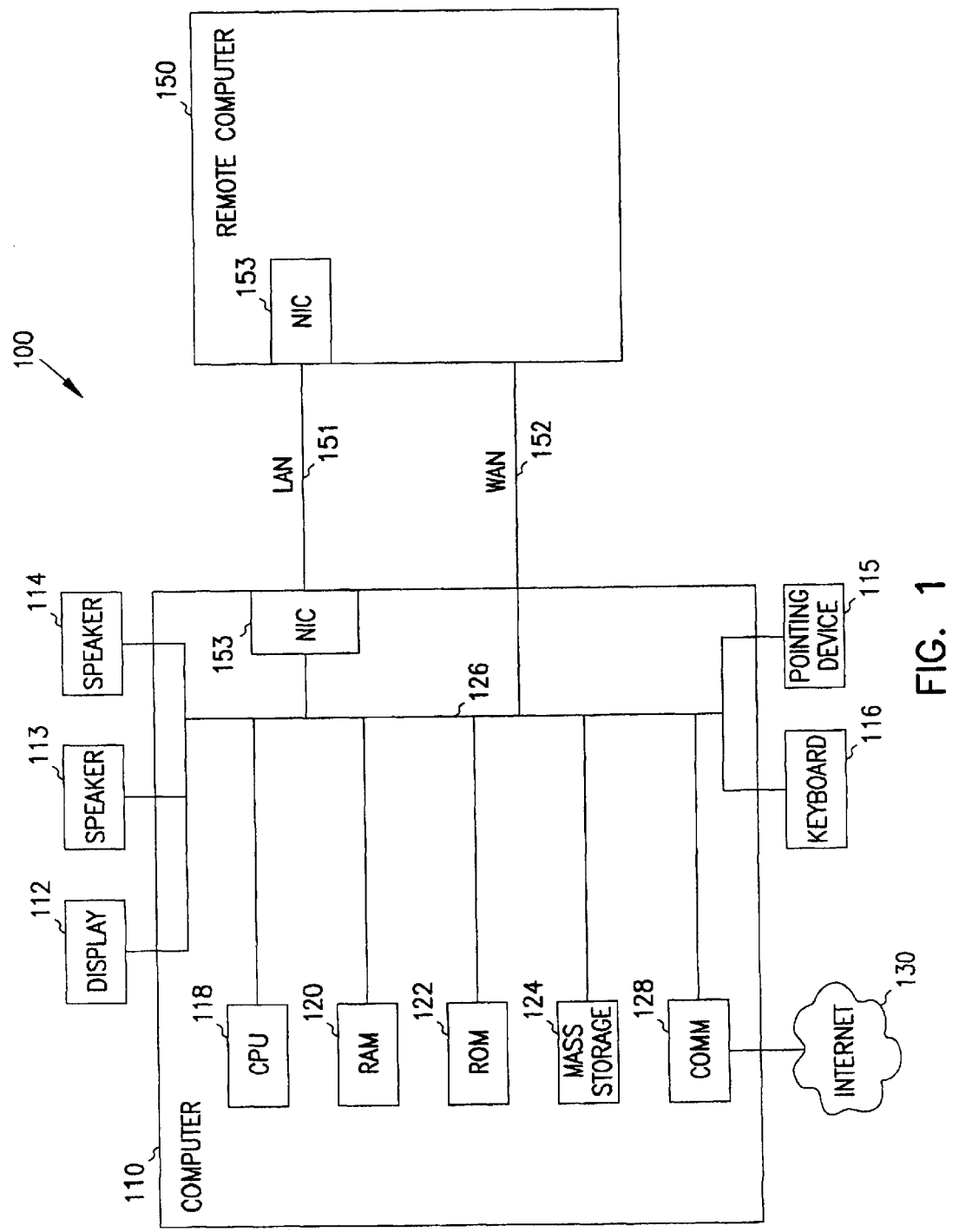
FIG. 1 is a block diagram of the hardware and operating environment in which different embodiments of the invention can be practiced.

FIG. 1 is a block diagram of the hardware and operating environment 100 in which different embodiments of the invention can be practiced. The description of FIG. 1 provides an overview of computer hardware and a suitable computing environment in conjunction with which some embodiments of the present invention can be implemented. Embodiments of the present invention are described in terms of a computer executing computer-executable instructions. However, some embodiments of the present invention can be implemented entirely in computer hardware in which the computer-executable instructions are implemented in read-only memory. One embodiment of the invention can also be implemented in client/server computing environments where remote devices that are linked through a communications network perform tasks. Program modules can be located in both local and remote memory storage devices in a distributed computing environment.

Computer 110 is operatively coupled to display device 112, pointing device 115, and keyboard 116. Computer 110 includes a processor 118, commercially available from Intel®, Motorola®, Cyrix® and others, random-access memory (RAM) 120, read-only memory (ROM) 122, and one or more mass storage devices 124, and a system bus 126, that operatively couples various system components including the system memory to the processing unit 118. Mass storage devices 124 are more specifically types of nonvolatile storage media and can include a hard disk drive, a floppy disk drive, an optical disk drive, and a tape cartridge drive. The memory 120, 122, and mass storage devices, 124, are types of computer-readable media. A user enters commands and information into the computer 110 through input devices such as a pointing device 115 and a keyboard 116. Other input devices (not shown) can include a microphone, joystick, game pad, satellite dish, scanner, or the like. The processor 118 executes computer programs stored on the computer-readable media. Embodiments of the present invention are not limited to any type of computer 110. In varying embodiments, computer 110 comprises a PC-compatible computer, a MacOS®-compatible computer or a UNIX®-compatible computer. The construction and operation of such computers are well known within the art.

Furthermore, computer 110 can be communicatively connected to the Internet 130 via a communication device 128. Internet 130 connectivity is well known within the art. In one embodiment, a communication device 128 is a modem that responds to communication drivers to connect to the Internet via what is known in the art as a "dial-up connection." In another embodiment, a communication device 128 is an Ethernet® or similar hardware (network) card connected to a local-area network (LAN) that itself is connected to the Internet via what is known in the art as a "direct connection" (e.g., T1 line, etc.).

Computer 110 can be operated using at least one operating environment to provide a graphical user interface including a user-controllable pointer. Such operating environments include operating systems such as versions of the Microsoft Windows® and Apple MacOS® operating systems well-known in the art. Embodiments of the present invention are not limited to any particular operating environment, however, and the construction and use of such operating environments are well known within the art. Computer 110 can have at least one web browser application program executing within at least one operating environment, to permit users of computer 110 to access intranet or Internet world-wide-web pages as addressed by Universal Resource Locator (URL) addresses. Such browser application programs include Netscape Navigator® and Microsoft Internet Explorer®.

Display device 112 permits the display of information, including computer, video and other information, for viewing by a user of the computer. Embodiments of the present invention are not limited to any particular display device 112. Such display devices include cathode ray tube (CRT) displays (monitors), as well as flat panel displays such as liquid crystal displays (LCD's). Display device 112 is connected to the system bus 126. In addition to a monitor, computers typically include other peripheral input/output devices such as printers (not shown), speakers, pointing devices and a keyboard. Speakers 113 and 114 enable the audio output of signals. Speakers 113 and 114 are also connected to the system bus 126. Pointing device 115 permits the control of the screen pointer provided by the graphical user interface (GUI) of operating systems such as versions of Microsoft Windows®. Embodiments of the present invention are not limited to any particular pointing device 115. Such pointing devices include mouses, touch pads, trackballs, remote controls and point sticks. Finally, keyboard 116 permits entry of textual information into computer 110, as known within the art, and embodiments of the present invention are not limited to any particular type of keyboard.

The computer 110 can operate in a networked environment using logical connections to one or more remote computers, such as remote computer 150. The logical connections are achieved by a communication device coupled to, or a part of, the computer 110. Embodiments of the present invention are not limited to a particular type of communications device. The remote computer 150 can be another computer, a server, a router, a network PC, a client, a peer device or other common network node. The logical connections depicted in FIG. 1 include a local-area network (LAN) 151 and a wide-area network (WAN) 152. Such networking environments are commonplace in offices, enterprise-wide computer networks, intranets and the Internet.

When used in a LAN-networking environment, the computer 110 and remote computer 150 are connected to the local network 151 through a network interface or adapter 153, which is one type of communications device. When used in a conventional WAN-networking environment, the computer 110 and remote computer 150 communicate with a WAN 152 through modems (not shown). The modem, which can be internal or external, is connected to the system bus 126. In a networked environment, program modules depicted relative to the computer 110, or portions thereof, can be stored in the remote memory storage device.

System Level Overview

Figure 2:
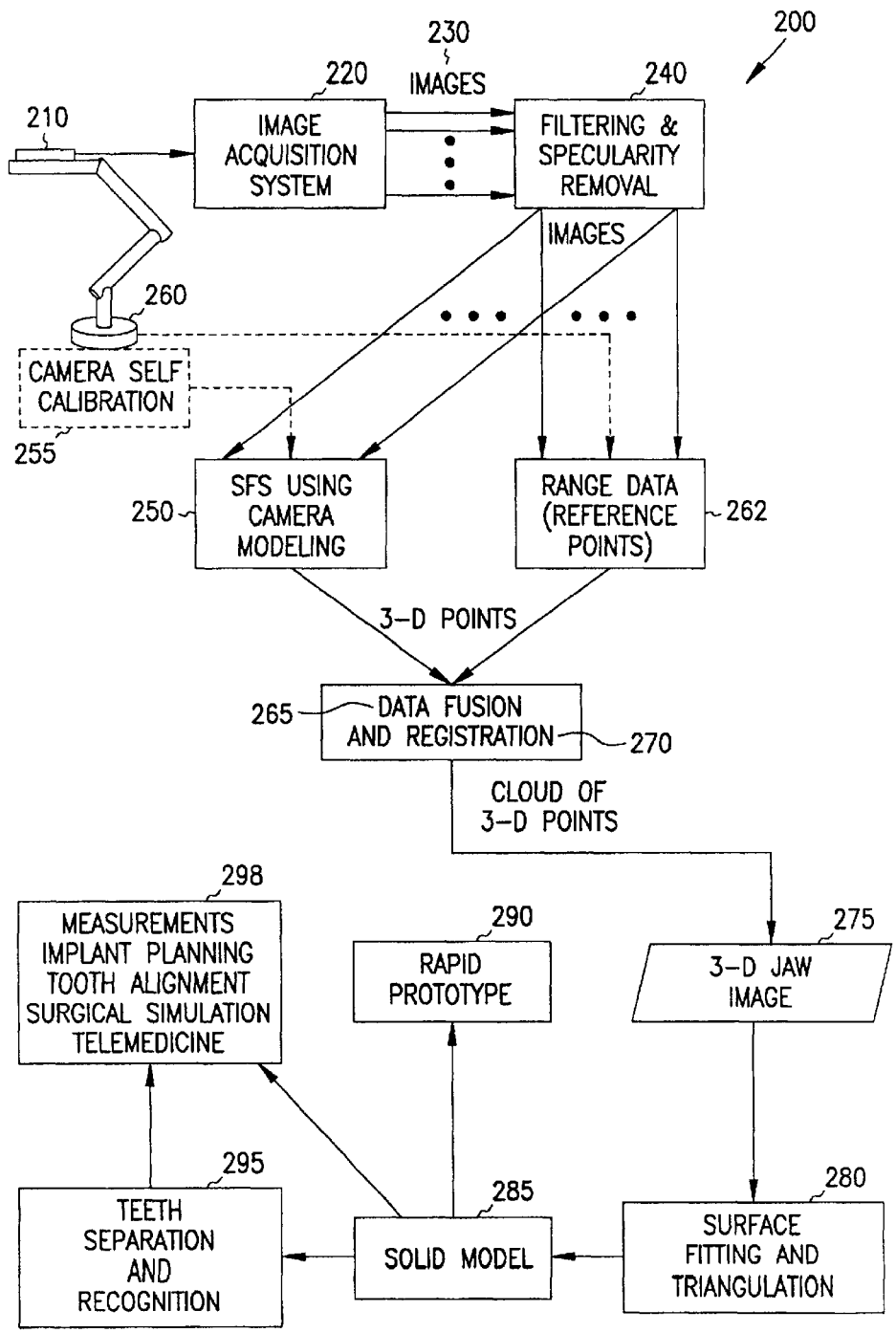
FIG. 2 is a diagram illustrating a system-level overview of an embodiment of the invention.

FIG. 2 is a block diagram that provides a system level overview of the operation of embodiments of the present invention. Embodiments of the invention are described as operating in a multi-processing, multi-threaded operating environment on a computer, such as computer 110 in FIG. 1.

System 200 includes a small intra-oral charge coupled device (CCD) camera 210 to enable the first stage of data acquisition 220. In one embodiment, the camera 210 includes a built-in white light, rigidly mounted on a five-link 3-D digitizer arm. The camera 210 is calibrated and then placed inside the oral cavity. The camera 210 acquires a set of overlapping images 230 $\{I_j|j=1,2,\ldots,J\}$ for various portions of the jaw such that $U_{j=1}I_j$ covers the entire jaw. The images 230 are preprocessed to reduce noise, sharpen edges, and remove specularity 240. Removing specularity 240 is improves the accuracy of the reconstructed surfaces using a shape-from-shading (SFS) process 250. In one embodiment of removing specularity, changes in the reflection map are removed from a luminance image by calculating the logarithmic gradient of the image 230 and thresholding at locations of abrupt chromaticity change. In another embodiment, median filtering is implemented to remove speckle noise from the images. Using a SFS process 250 that accounts for the camera perspective projection 255, J sets of 3-D points are computed. To obtain accurate metric measurements, range data 262 is obtained using the five-link digitizer 260. The range data comprises reference points on the jaw. Fusion 265 of the range data and the SFS output provides accurate metric information that can be used later for orthodontic measurements and implant planning. System 200 also includes a registration 270 technique that merges the resulting 3-D points to obtain a complete 3-D description of the jaw 275. The 3-D description 275 is transformed into patches of free form surfaces using a triangulation process 280. The triangulation process 280 enables optional development of a 3-D solid model 285 for visualization. Optionally, a cast 290 is fabricated from the 3-D description 275 via rapid prototyping. Further optional processing of the digital model 275 includes tooth separation 295, force analysis, implant planning, and surgical simulation 298.

The system level overview of the operation of an embodiment of the invention has been described in this section of the detailed description. While the invention is not limited to any particular camera 210, image acquisition system 220, data fusion 265 and registration process 270, triangulation process 280, and cast 290, for sake of clarity a simplified camera 210, image acquisition system 220, data fusion 265 and registration process 270, triangulation process 280, and cast 290, has been described.

Methods of an Embodiment of the Invention

In the previous section, a system level overview of the operation of an embodiment of the invention was described. In this section, the particular methods of such an embodiment are described by reference to a series of flowcharts. Describing the methods by reference to a flowchart enables one skilled in the art to develop such programs, firmware, or hardware, including such instructions to carry out the methods on suitable computers (the processor of the computers executing the instructions from computer-readable media). Similarly, the methods performed by the server computer programs, firmware, or hardware are also composed of computer-executable instructions. Methods 300–500 and 700 are performed by a program executing on, or performed by firmware or hardware that is a part of, a computer, such as computer 110 in FIG. 1

Figure 3:
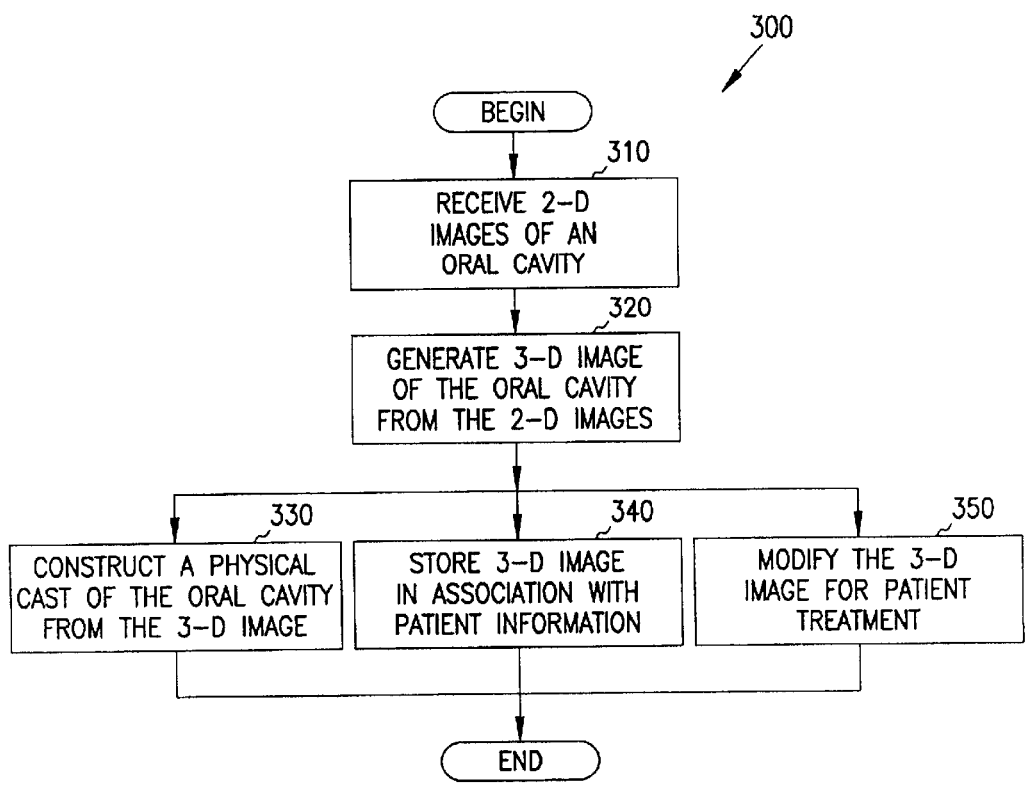
FIG. 3 is a flowchart of a method for dental imaging, according to an embodiment of the invention.

FIG. 3 is a flowchart of a method 300 for dental imaging, according to an embodiment of the invention.

Method 300 includes receiving 310 a plurality of two-dimensional (2-D) images of an oral cavity. In varying embodiments, the oral cavity is a mammalian oral cavity and/or a human oral cavity. In other embodiments, the plurality of 2-D images are a plurality of 2-D optical images.

Thereafter, method 300 includes generating 320 at least one three-dimensional (3-D) image of the oral cavity from the plurality of 2-D images.

Optionally, method 300 also includes constructing 330 a physical cast of the oral cavity from the 3-D image. In varying embodiments, the physical cast is a plastic cast formed by a rapid prototyping machine, or a plaster cast.

Optionally, method 300 includes storing 340 the 3-D image in association with patient information. For example, the 3-D image is stored in a database of patient records.

Optionally, method 300 further includes modifying 350 the 3-D image in accordance with a proposed or suggested orthodontic or dental treatment of the patient.

In another embodiment of method 300, the 2-D images that are received in action 310, are beforehand generated from a common reference point in 3-D space.

Figure 4:
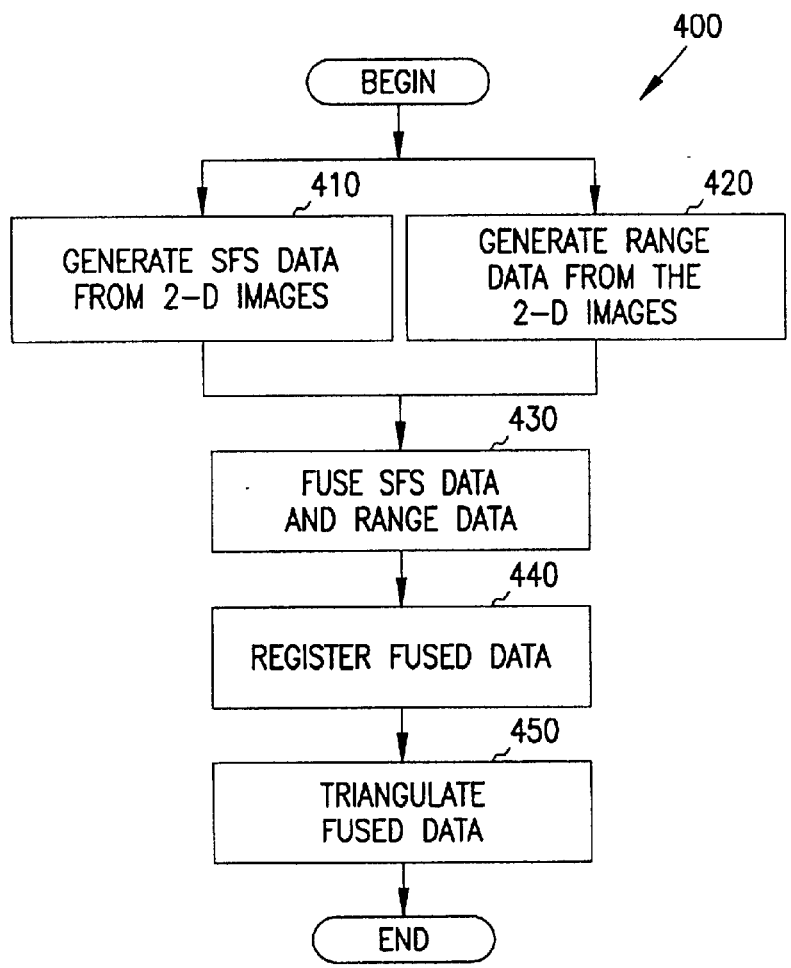
FIG. 4 is a flowchart of a method for generating a 3-D image of the oral cavity from the plurality of 2-D images, according to an embodiment of the invention.

FIG. 4 is a flowchart of a method 400 for generating a 3-D image of the oral cavity from the plurality of 2-D images, according to an embodiment of the invention.

Method 400 includes generating 410 shape-from-shading (SFS) data from the plurality of 2-D images using a shape-from-shading process, the shape-from-shading data comprising a first plurality of 3-D points. Generating SFS data is disclosed in further detail in method 500 in FIG. 5.

Method 400 also includes generating 420 range data comprising a second plurality of 3-D points from the plurality of 2-D images using a range-data process.

Method 400 further includes fusing 430 the range data to the shape-from-shading data, yielding fused data comprising a third plurality of 3-D points. Fusing 430 is disclosed in further detail in method 700 in FIG. 7.

Thereafter, method 400 includes registering 440 the fused data, yielding registered data comprising a fourth plurality of 3-D points.

Subsequently, method 400 includes triangulating 450 the registered data, yielding the at least one 3-D image of the oral cavity.

Figure 5:
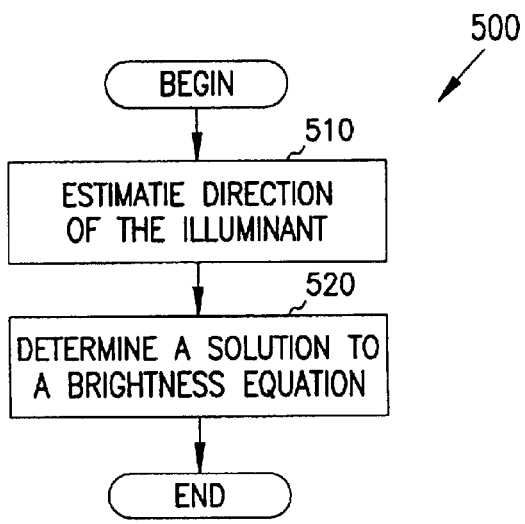
FIG. 5 is a flowchart of a method for generating shape-from-shading data, according to an embodiment of the invention.

FIG. 5 is a flowchart of a method 500 for generating shape-from-shading data, according to an embodiment of the invention.

SFS assumes that the surface orientation at a point M on a surface S is determined by the unit vector perpendicular to the plane tangent to S at M. Under the assumption of orthographic projections, the elemental change in the depth Z at an image point (x,y) can be expressed as $$\delta z \approx \frac{\partial Z}{\partial x}\delta x + \frac{\partial Z}{\partial y}\delta y.$$

The partial derivatives are called surface gradients (p,q). The normal to a surface patch is related to the surface gradient by $n=(p,q,1)$. Assuming that surface patches are homogeneous and uniformly lit by distant light sources, the brightness $E(x,y)$ seen at the image plane often depends only on the orientation of the surface. This dependence of brightness on surface orientation can be represented as a function $R(\cdot)$ defined on the Gaussian sphere. Thus, the SFS problem is formulated as finding a solution to the brightness equation: $E(x,y)=R(p,q,L)$, where $R(p,q,L)$ is the surface reflectance map and L is the illuminant direction.

Method 500 includes estimating 510 the direction of the illuminant from the plurality of 2-D images, in reference to camera intrinsic parameters.

In the present invention, a white light beam is built in the CCD camera, yielding a valid assumption that the illuminant direction is known. However, an assumption of orthographic projection is not adequate for the dental application because the camera is very close to the object. Conventional SFS methods using perspective projection ignore the camera extrinsic parameters, hence cannot provide metric information of the depth. In the present invention, the CCD camera is calibrated and the camera parameters are used in the SFS method to obtain a metric representation of the teeth and gum surfaces. To calibrate the camera, the relation between the 3D point M={X,Y,Z} and the corresponding image coordinates m={x,y} is written as; $s\vec{m}=\vec{PM}$ where s is a scalar, $\vec{m}$ and $\vec{M}$ are the extended vectors $[m^T 1]^T$ and $[M^T 1]^T$, and P is called the camera calibration matrix. In general, P=A [R,t] where A is a matrix containing all the camera intrinsic parameters and R,t are the rotation matrix and translation vector. The matrix P has 12 elements but has only 11 degrees of freedom because it is defined up to a scale factor.

The standard method of calibration is to use an object with known size and shape and extract the reference points from the object image. It can be shown that given N points (N>=6) in general positions, the camera can be calibrated. The perspective projection matrix P can be decomposed as [Bb] where B is a 3×3 matrix and b is a 3×1 vector such that:

TABLE 1

| $s\vec{m} = BM + b$ |
|---| or,

TABLE 2

| $M = B^{-1}(s\vec{m} - b) = f(s(x,y))$ |
|---|

This last equation represents a line in the 3D space corresponding to the visual ray passing through the optical center and the projected point m. By finding the scalar s, $f(s(x,y))$ will define a unique 3D point M on the object. The surface normal at M is defined to be the cross product of the two gradient vectors $$p = \frac{df(s(x, y))}{dx}, q = \frac{df(s(x, y))}{dy}.$$

The surface reflectance $R(.)$ becomes a function of the scalars defined in The equation in table 1, i.e.,

TABLE 7

| $\frac{d\vec{v}}{ds_{x,y}} = B^{-1}\vec{m} \times B^{-1}(0, s_{x,y-1}, 0)^t + B^{-1}(s_{x-1,y}, 0, 0)^t \times B^{-1}\vec{m}$ |
|---|
| where $v = p \times q$. |

Method 500 also includes determining 520 a solution to a brightness equation from the direction of the illuminant, yielding the shape-from-shading data comprising a first plurality of 3-D points.

The formulation of the SFS problem becomes finding the scalar s that solves the brightness equation $g(s)=E(x,y)\Box R(s)=0$. In one embodiment, the brightness equation is solved using a Taylor's series expansion and applying a Jacoby iterative method [ ]. After n iterations, for each point (x,y) in the image, $s_{x,y}{}^n$ is given as follows

TABLE 4

$$s_{x,y}^n = s_{x,y}^{n-1} + \frac{-g(s_{x,y}^{n-1})}{\frac{d}{ds_{x,y}}g(s_{x,y}^{n-1})}$$

where,

TABLE 5

$$\frac{d}{ds_{x,y}}g(s_{x,y}) = -\frac{dN}{ds_{x,y}} \cdot \frac{L}{|L|}$$

TABLE 6

$$\frac{dN}{ds_{x,y}} = \frac{dv}{ds_{x,y}} \frac{1}{\sqrt{v^t v}} - \frac{v}{\sqrt{(v^t v)^3}} \left( v^t \frac{dv}{ds_{x,y}} \right)$$

TABLE 7

$$\frac{dv}{ds_{x,y}} = B^{-1}\vec{m} \times B^{-1}(0, s_{x,y-1}, 0)^t + B^{-1}(s_{x-1,y}, 0, 0)^t \times B^{-1}\vec{m}$$

where $v = p \times q$.

Figure 6:
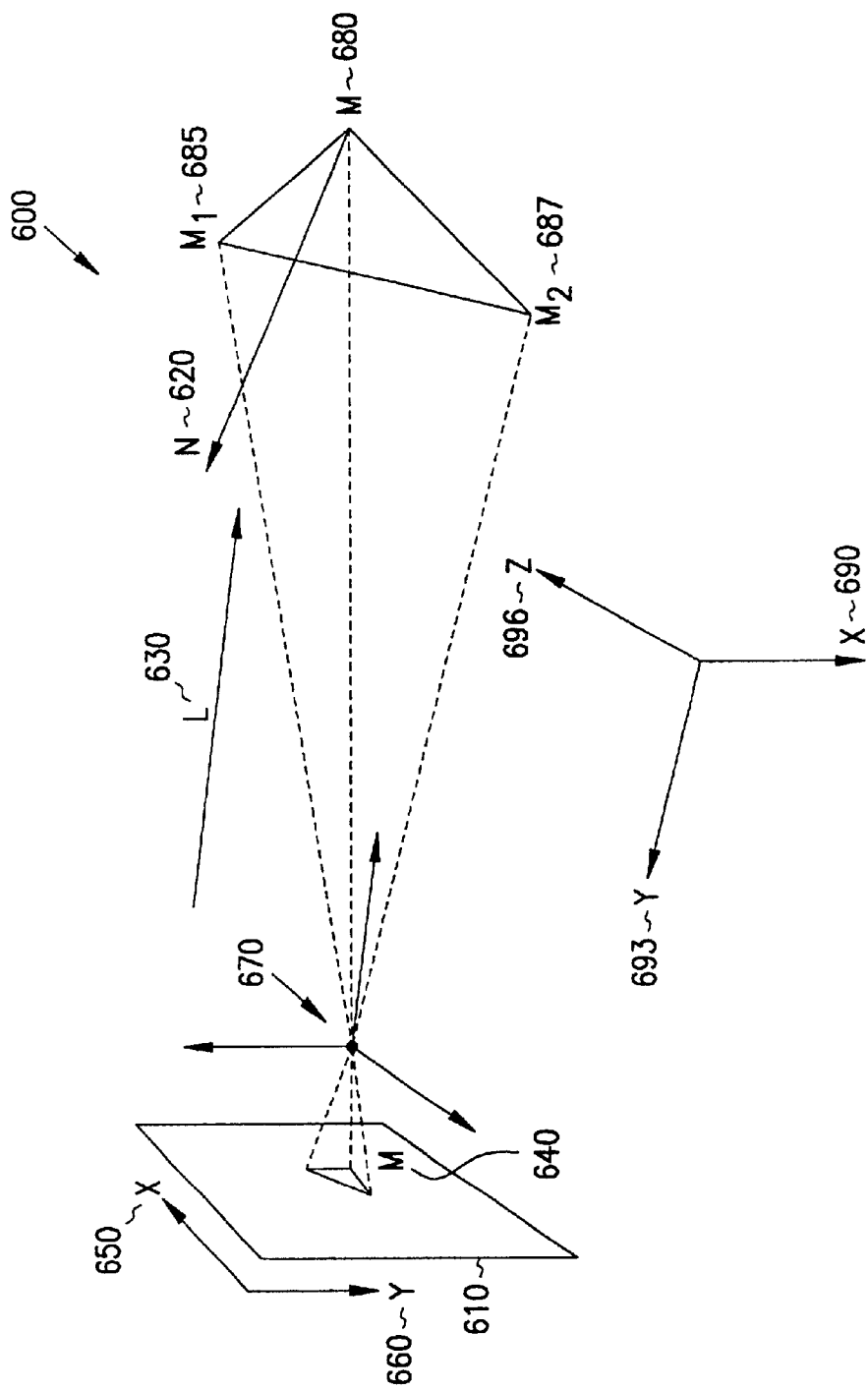
FIG. 6 is a diagram of surface triangulation, according to an embodiment of the invention.

FIG. 6 is a diagram 600 of surface triangulation, according to an embodiment of the invention.

Diagram 600 includes the image plane 610 as a set of triangular patches each with a normal N 620, the dot product of the light direction L 630 and the normal N 620 is called the reflectance which determines the image intensity at the corresponding pixel location m 640. Image plane 610 is described as having 2-D coordinates x 650 and y 660. When pixel location m 640 is projected beyond optical center 670, in light direction L 630, the projection yields form M 680 having points $M_1$ 685 and $M_2$ 687. The diagram is also described in relation to 3-D coordinates X 690, Y 693, and Z 686.

In another embodiment of method 500, method 500 is described in terms of the FIG. 6 by:

TABLE 8

$$M = B^{-1}\left(s_{x,y}\begin{pmatrix}x\\y\\1\end{pmatrix} - b\right)$$

$$M_1 = B^{-1}\left(s_{x-1,y}\begin{pmatrix}x-1\\y\\1\end{pmatrix} - b\right)$$

$$M_2 = B^{-1}\left(s_{x,y-1}\begin{pmatrix}x\\y-1\\1\end{pmatrix} - b\right)$$

$$p = M - M_1$$

TABLE 9

$$= B^{-1}(s_{x,y} - s_{x-1,y})\begin{pmatrix}x\\y\\1\end{pmatrix} + B^{-1}s_{x-1,y}\begin{pmatrix}1\\0\\0\end{pmatrix}$$

$$q = M - M_2$$

TABLE 10

$$= B^{-1}(s_{x,y} - s_{x,y-1})\begin{pmatrix}x\\y\\1\end{pmatrix} + B^{-1}s_{x,y-1}\begin{pmatrix}1\\0\\0\end{pmatrix}$$

A unit normal N to the patch formed by M, $M_1$, and $M_2$ is calculated as follows:

TABLE 11

$$N = \frac{p \times q}{\|p \times q\|}$$

A reflection function defined by the SFS is:

TABLE 12

$$R(\cdot) = \frac{N \cdot L}{\|L\|}$$

Thus, the SFS brightness equation becomes:

TABLE 13

$$g(s_{x,y}) = E(x, y) - \frac{N \cdot L}{\|L\|}$$

The solution to the SFS problem is to find $s_{x,y}$ such that g(.) is minimized. Using Taylor expansion and Jacoby iterative methods, s(x,y) can be found by iteration as follows:

TABLE 14

$$s_{x,y}^n = s_{x,y}^{n-1} + \frac{-g\left(s_{x,y}^{n-1}\right)}{\frac{d}{ds_{m,y}}g(s_{x,y}^{n-1})}$$

TABLE 15

$$\frac{d}{ds_{x,y}}g(s_{x,y}) = \frac{dN}{ds_{x,y}} \cdot \frac{L}{|L|}$$

TABLE 16

Let $N = \frac{v(s)}{\sqrt{v(s)^t v(s)}}$ where $v(s) = p \times q$

TABLE 17

$$\frac{d\mathbf{N}}{ds_{x,y}} = \frac{d\mathbf{v}}{ds_{x,y}} \frac{1}{\sqrt{\mathbf{v}^t\mathbf{v}}} - \frac{\mathbf{v}}{\sqrt{(\mathbf{v}^t\mathbf{v})^3}} \left( \mathbf{v}^t \frac{d\mathbf{v}}{ds_{x,y}} \right)$$

$$\frac{d\mathbf{v}}{ds_{x,y}} = \frac{d}{ds_{x,y}}(\mathbf{p} \times \mathbf{q})$$

$$= \frac{d\mathbf{p}}{ds_{x,y}} \times \mathbf{q} + \mathbf{p} \times \frac{d\mathbf{q}}{ds_{x,y}}$$

$$\frac{d\mathbf{p}}{ds_{x,y}} = \frac{d\mathbf{q}}{ds_{x,y}} = B^{-1} \begin{pmatrix} x \\ y \\ 1 \end{pmatrix}$$

$$\frac{d\mathbf{v}}{ds_{x,y}} = B^{-1} \begin{pmatrix} x \\ y \\ 1 \end{pmatrix} \times B^{-1} \begin{pmatrix} 0 \\ s_{x,y}-1 \\ 0 \end{pmatrix} + B^{-1} \begin{pmatrix} s_{x-1,y} \\ 0 \\ 0 \end{pmatrix} \times B^{-1} \begin{pmatrix} x \\ y \\ 1 \end{pmatrix}$$

The actions involved in the implementation include reading image E(x,y), light direction L, and camera parameters (B,b). Initializing $s_{x,y}$=0.01. $\square \forall x,y$ get p and q as shown in the equations in tables 9 and 10. Calculating N as shown in equation in table 11. Obtaining the error using the brightness equation in table 13. Estimating the new $s_{x,y}$ using the equations in tables 14, 15, 16, and 17. Repeating the actions of $\forall$, calculating and estimating, until $\max_{x,y}|g(S_{x,y})|<\epsilon$ where $\epsilon$ is a predefined positive threshold. Thereafter, recovering the surface 3-D points using equation in table 8, and constructing triangular patches as shown in FIG. 6.

Figure 7:
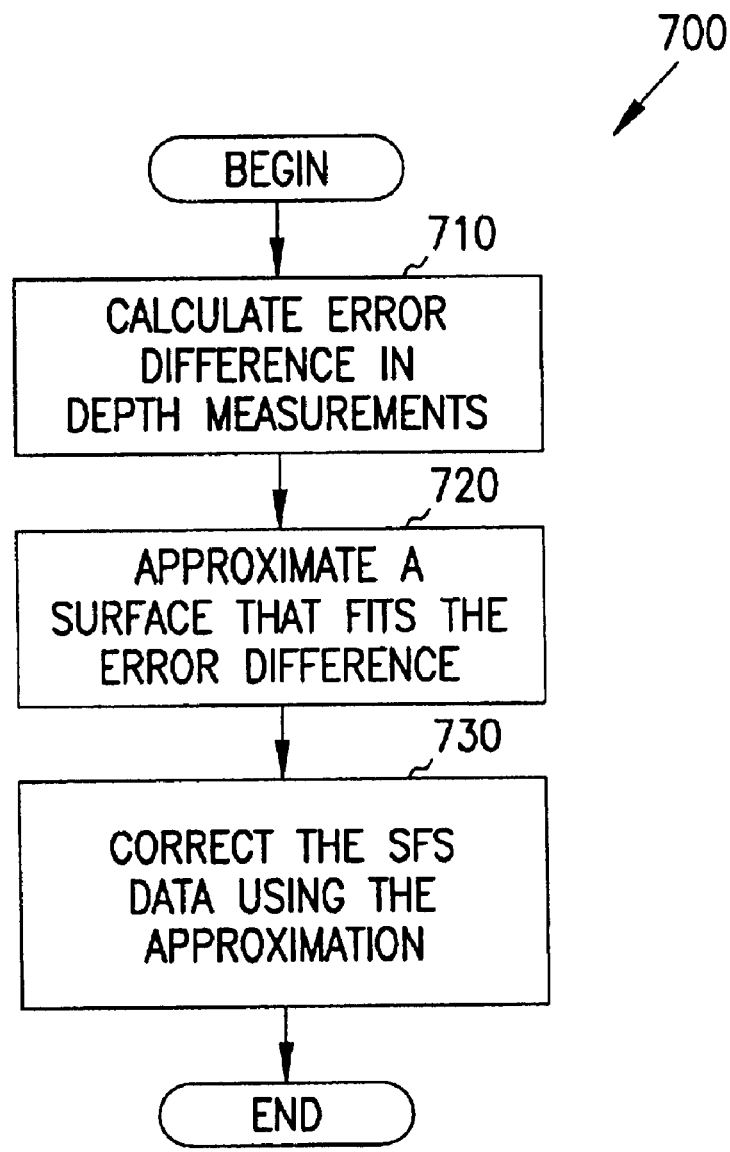
FIG. 7 is a flowchart of a method for fusing the range data to the shape-from-shading data, according to an embodiment of the invention.

FIG. 7 is a flowchart of a method 700 for fusing the range data to the shape-from-shading data, as in the fusing action 430 in FIG. 4, according to an embodiment of the invention.

The most important information for reconstructing an accurate 3-D visible surface, which is missing in shape from shading, is the metric measurement. Shape from shading also suffers from the discontinuities due to highly textured surfaces and different albedo. The integration of the dense depth map obtained from SFS with sparse depth measurements obtained from a coordinate measurement machine (CMM) for the reconstruction of 3-D surfaces with accurate metric measurements has two advantages. First, the integration removes ambiguity of the 3-D visible surface discontinuities produced by shape from shading. Second, the integration complements missing metric information in the shape from shading. The integration process, as depicted in FIG. 7, includes the following stages. First, calculating 710 the error difference in the available depth measurements between the two sets of sensory data. Thereafter, approximating 720 a surface that fits this error difference. Subsequently, correcting 730 the shape from shading.

Method 700 includes calculating 710 the error difference in available depth measurements of the range data and the shape-from-shading data.

A multi-layer neural network is used for the surface approximation process since neural networks was shown to be more robust in terms of complexity, speed and accuracy than other computational approaches (e.g., regularization techniques). The learning algorithm applied is an extended Kalman-filter learning technique because of fast computation of weights generated by Kalman-filter. The x- and y-coordinates of the data points are the input to the network, while the error in the depth value at the point (x,y) is the desired response. The error difference between the SFS and the range measurements and their x-y coordinates are used to form the training set. The input to the network is the x-y coordinates and the output is the error difference at that coordinate.

Method 700 includes approximating 720 a surface the fits the error difference, yielding an approximated surface.

Once training is accomplished, the neural network provides the approximated smooth surface that contains information about the errors in the shape from shading at the locations with no range data.

Method 700 includes correcting 730 the shape-from-shading data from the approximated surface, yielding fused data comprising a third plurality of 3-D points.

This approximated surface is then added to the SFS. The result is the 3-D surface reconstruction that contains accurate metric information about the visible surface of the sensed 3-D object. The output of the fusion algorithm to each image is a set of 3-D points describing the teeth surfaces in this segment. To compensate for some digitizer inaccuracy in determining the camera location in space and the occasional patient movement, The present invention in some embodiments includes a 3-D registration technique to link the 3-D points of all the segments to produce one set of 3-D points describing the whole jaw surface.

In one embodiment, methods 300–500 and 700 are implemented as a computer data signal embodied in a carrier wave, that represents a sequence of instructions which, when executed by a processor, such as processor 118 in FIG. 1, cause the processor to perform the respective method.

In another embodiment, methods 300–500 and 700 are implemented as a computer-readable medium having computer-executable instructions to cause a computer, such as computer 110, to perform the respective method.

Apparatus Implementation

Figure 8:
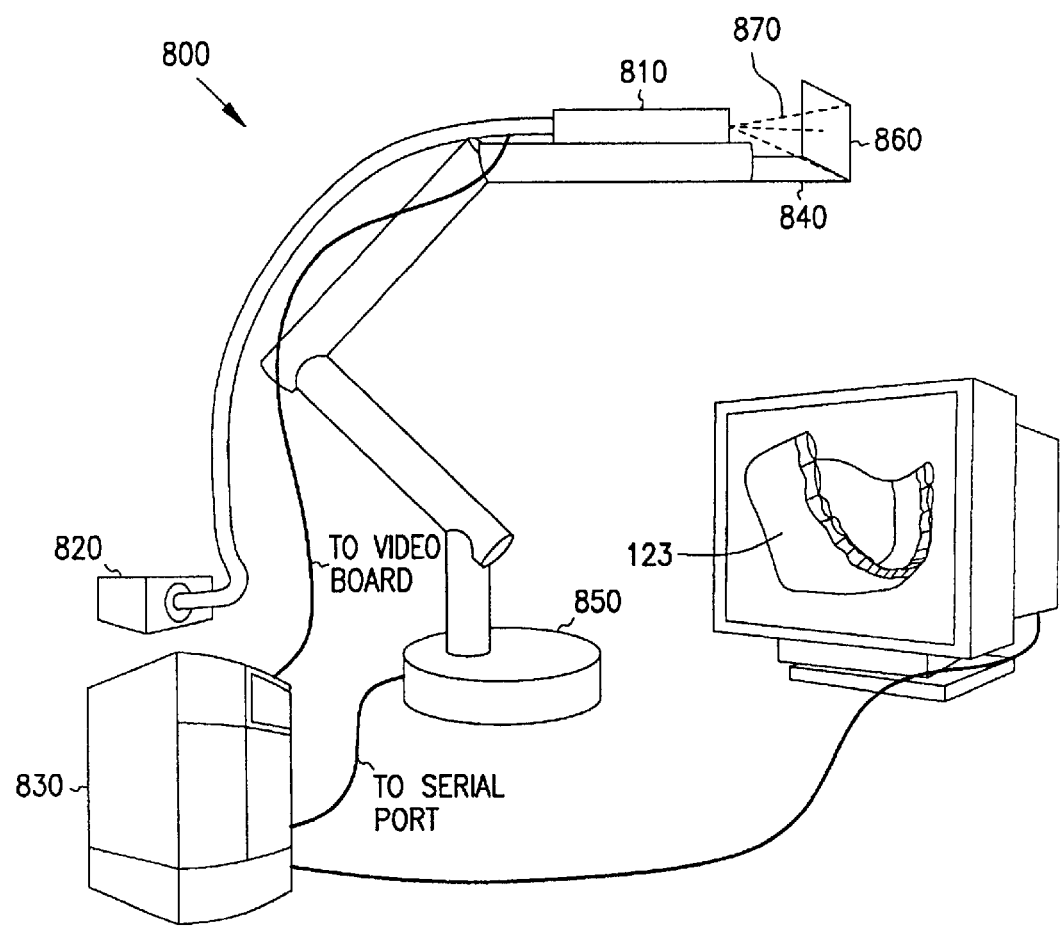
FIG. 8 is a block diagram of an apparatus for generating a three-dimensional digital image of a jaw, according to an embodiment of the invention.
Figure 9:
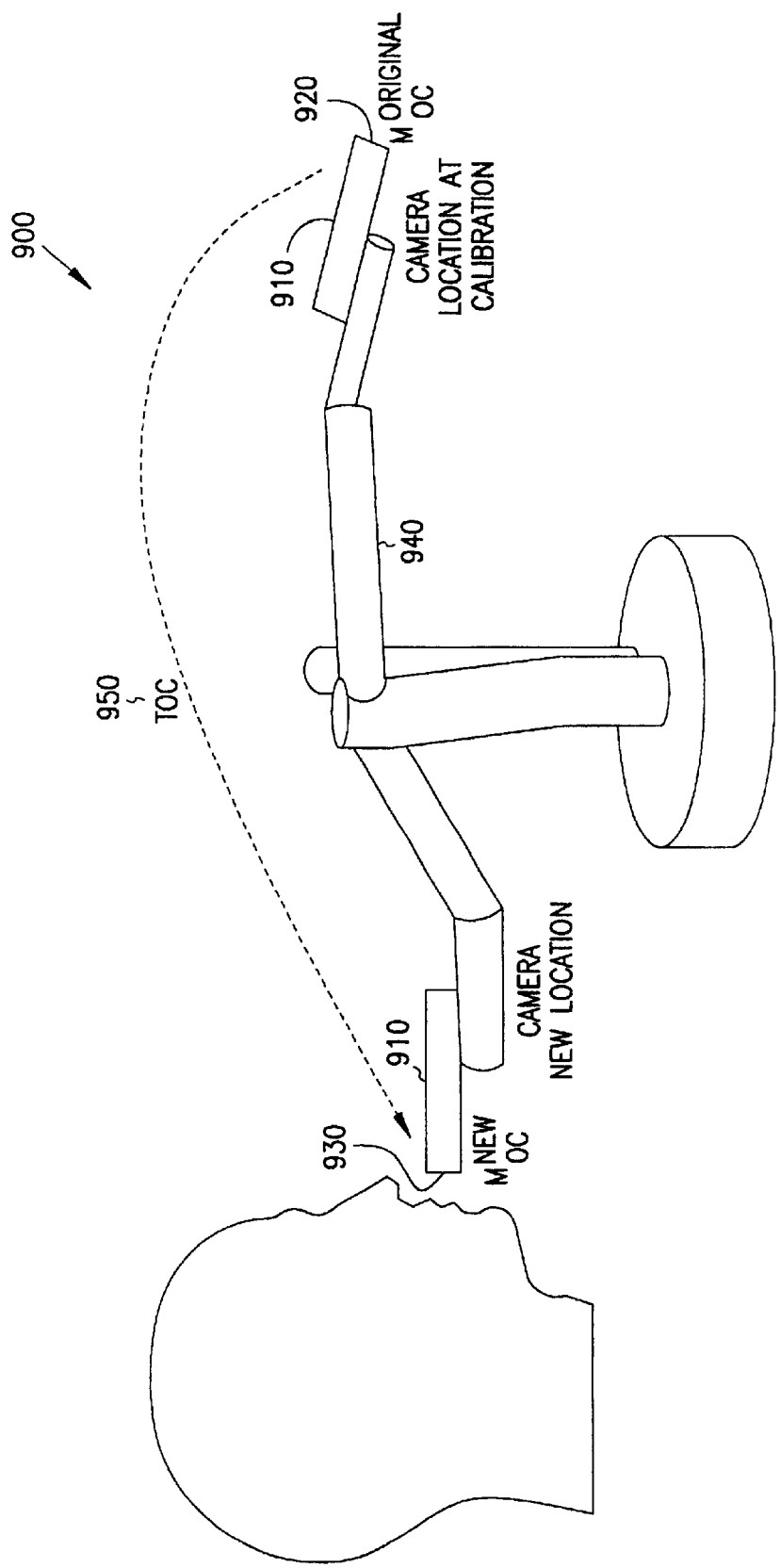
FIG. 9 is a block diagram of an apparatus involved in calibrating a charge coupled device camera, according to an embodiment of the invention.

Referring to FIG. 8–9, a particular implementation of the invention is described in conjunction with the hardware and operating environment 100, the system overview in FIG. 2 and the methods described in conjunction with FIGS. 3–5 and 7.

FIG. 8 is a block diagram of an apparatus 800 for generating a three-dimensional digital image of a jaw, according to an embodiment of the invention.

Apparatus 800 includes a ⅓ inch charge coupled device (CCD) color camera 810, such as camera 210 in FIG. 2. The camera 810 has 768H×494V effective picture elements. In one embodiment, the camera also includes a 5.5 mm lens. Apparatus 800 also includes a 150 watt direct current regulated white light source 820. Through a fiber optic bundle (not shown) that surrounds the CCD camera 810, the light source 820 illuminates an oral cavity with a stable white light. The light intensity is manually adjustable to control a shading effect. Apparatus 800 also includes a computer 830, such as computer 110 in FIG. 1, that hosts the software required for the data processing, reconstruction and visualization of the three-dimensional (3-D) jaw model, as described in methods 300–500 and 700. Computer 830 also includes a 3-D digitizer 850, capable of digitizing a working space up to 1.27 m (sphere) with a sampling rate of 1000 points/second. 3-D digitizer 850 is also shown as five-link digitizer 260 in FIG. 2.

The CCD camera 810 is mounted on a stylus 840 of the 3-D digitizer 850 and its focal distance 870 is adjusted such that the image will be in focus only when the stylus tip touches a tooth surface. An image plane 860 is normal to the stylus and the stylus tip is at pixel (0,0). Apparatus 800 also includes a display 880, such as display 112 in FIG. 1 to display the 3-D jaw model The CCD camera 810 is calibrated as shown in FIG. 9.

FIG. 9 is a block diagram of an apparatus 900 involved in calibrating a charge coupled device camera, according to an embodiment of the invention. A coordinates measuring system is used to find the transformation matrix $T_{oc}$ 950 between the optical center $M_{oc}$ of the camera at the calibration time 920 and the new location 930 while acquiring the images. This transformation matrix is used to obtain the new camera perspective projection matrix.

Camera 910 calibration is performed once before using the camera 910. Where the camera 910 is stationary, the camera 910 does not need to be re-calibrated again. Yet in some embodiments, the camera 910 will be moving. Camera 910 movement requires the recalculation of the perspective projection matrix. However, as the camera 910 is mounted on a coordinates measuring system, the location of the optical center $M_{oc}$ can be tracked as the camera 910 moves from original optical center $M_{oc}$ 930 to new optical center $M_{oc}$ 930, and the camera 910 perspective projection can be recalculated.

The five degrees of freedom provided by an arm 940 enables the acquisition of a sequence of intra-oral images covering the upper/lower jaw. Also, with each image, the camera 910 location in the 3-D space is measured. The perspective projection matrix is re-adjusted and the location and direction of the first pixel in the image are included. This information is used in the data fusion and registration phase to reference the image plane in the workspace.

In a computer-readable program embodiment, programs implementing methods 300–500 and 700 can be structured in an object-orientation using an object-oriented language such as Java, Smalltalk or C++, and the programs can be structured in a procedural-orientation using a procedural language such as COBOL or C. The software components communicate in any of a number of means that are well-known to those skilled in the art, such as application program interfaces (A.P.I.) or interprocess communication techniques such as remote procedure call (R.P.C.), common object request broker architecture (CORBA), Component Object Model (COM), Distributed Component Object Model (DCOM), Distributed System Object Model (DSOM) and Remote Method Invocation (RMI). The components execute on as few as one computer as in computer 110 in FIG. 1, or on at least as many computers as there are components.

Reconstructing the 3-D model of the human jaw includes by capturing a sequence of video images using a small intra-oral CCD camera. These images are preprocessed to remove specularity. Reference points are obtained using the coordinate measurement machine (CMM) system. The range data are fused to the shape from shading (SFS) output and then registration takes place. A cloud of points representing the jaw is obtained and, by triangulation, a solid digital model is formed. This model is optionally reproduced using a rapid prototype machine. Further analysis and orthodontics application can be performed on the digital model.

Conclusion

Systems and methods of a model-based vision system for dentistry that assists in diagnosis, treatment planning and surgical simulation have been described. Although specific embodiments have been illustrated and described herein, it will be appreciated by those of ordinary skill in the art that any arrangement which is calculated to achieve the same purpose may be substituted for the specific embodiments shown. This application is intended to cover any adaptations or variations of the present invention. One of ordinary skill in the art will appreciate that the invention can be implemented in a procedural design architecture, an object-oriented architecture, or any other design architecture that provides the required relationships.

The present invention includes an integrated computer vision system that constructs a three-dimensional (3-D) model of the patient's dental occlusion using an intra-oral video camera. A modified shape from shading (SFS) technique, using perspective projection and camera calibration, extracts the 3-D information from a sequence of two-dimensional (2-D) images of the jaw. Data fusion of range data and 3-D registration techniques develop the complete jaw model. Triangulation is then performed, and a solid 3-D model is reconstructed.

In particular, one of skill in the art will readily appreciate that the names of the methods and apparatus are not intended to limit embodiments of the invention. Furthermore, additional methods and apparatus can be added to the components, functions can be rearranged among the components, and new components to correspond to future enhancements and physical devices used in embodiments of the invention can be introduced without departing from the scope of embodiments of the invention. One of skill in the art will readily recognize that embodiments of the invention are applicable to future communication devices, different file systems, and new data types.

The terminology used in this application with respect to is meant to include all object-oriented, database and communication environments and alternate technologies which provide the same functionality as described herein. Therefore, it is manifestly intended that this invention be limited only by the following claims and equivalents thereof.

We claim:

1. A computerized method for dental imaging comprising:
   receiving a plurality of two-dimensional images of a oral cavity; and
   generating at least one three-dimensional image of the oral cavity from the plurality of two-dimensional images, including:
   generating shape-from-shading (SFS) data using the plurality of two-dimensional images;
   generating range data using a distribution arm; and
   processing the SFS data and the range data to generate the at least one three-dimensional image;
   wherein processing the SFS data and the range data to generate that at least one three-dimensional image comprises:
   fusing the range data to the shape-from-shading data, yielding fused data comprising a third plurality of three-dimensional points;
   registering the fused data, yielding registered data comprising a fourth plurality of three-dimensional points; and
   triangulating the registered data, yielding the at least one three-dimensional image of the oral cavity.

2. The computerized method of claim 1, wherein the plurality of two-dimensional images further comprises a plurality of two-dimensional optical images.

3. The computerized method of claim 1, further comprising:
   constructing a physical cast of the oral cavity from the three-dimensional image.

4. The computerized method of claim 1, further comprising:
   generating the plurality of two-dimensional images of the oral cavity from a common reference point in three-dimensional space.

5. The computerized method of claim 1, wherein the generating shape-from-shading data further comprises:
  estimating the direction of the illuminant from the plurality of two-dimensional images, in reference to camera intrinsic parameters; and
  determining a solution to a brightness equation, yielding the shape-from-shading data comprising a first plurality of three-dimensional points.

6. The computerized method of claim 1, wherein the fusing the range data to the shape-from-shading data further comprises:
  calculating an error difference in available depth measurements of the range data and the shape-from-shading data;
  approximating a surface that fits the error difference, yielding an approximated surface; and
  correcting the shape-from-shading data from the approximated surface, yielding fused data comprising a third plurality of three-dimensional points.

7. A computer-readable medium having computer-executable instructions to cause a computer to perform a method comprising:
  receiving a plurality of two-dimensional optical images of an oral cavity; and
  generating at least one three-dimensional image of the oral cavity from the plurality of two-dimensional images, including:
    generating shape-from-shading (SFS) data using the plurality of two-dimensional images;
    generating and range data using a digitizer arm; and
    processing the SFS data and the range data to generate the at least one three-dimensional image;
  wherein processing the SFS data and the range data to generate the at least one three-dimensional image comprises:
    fusing the range data to the shape-from-shading data, yielding fused data comprising a third plurality of three-dimensional points;
    registering the fused data, yielding registered data comprising a fourth plurality of three-dimensional points; and
    triangulating the registered data, yielding the at least one three-dimensional image of the oral cavity.

8. The computerized method of claim 7, further comprising: constructing a physical cast of the oral cavity from the three-dimensional image.

9. The computerized method of claim 7, further comprising:
  generating the plurality of two-dimensional images of the oral cavity from a common reference point in three-dimensional space.

10. The computerized method of claim 7, wherein the generating shape-from-shading data further comprises:
  estimating the direction of the illuminant from the plurality of two-dimensional images, in reference to camera intrinsic parameters; and
  determining a solution to a brightness equation, yielding the shape-from-shading data comprising a first plurality of three-dimensional points.

11. The computerized method of claim 7, wherein the fusing the range data to the shape-from-shading data further comprises:
  calculating an error difference in available depth measurements of the range data and the shape-from-shading data;
  approximating a surface that fits the error difference, yielding an approximated surface; and
  correcting the shape-from-shading data from the approximated surface, yielding fused data comprising a third plurality of three-dimensional points.

12. A three-dimensional digital image of a human oral cavity produced by the process comprising:
  generating a plurality of two-dimensional optical images of the oral cavity from a common reference point in three-dimensional space;
  generating shape-from-shading data from the plurality of two-dimensional images using a shape-from-shading process, the shape-from-shading data comprising a first plurality of three-dimensional points;
  generating range data comprising a second plurality of three-dimensional points from the plurality of two-dimensional images using a range-data process;
  fusing the range data to the shape-from-shading data, yielding fused data comprising a third plurality of three-dimensional points;
  registering the fused data, yielding registered data comprising a fourth plurality of three-dimensional points; and
  triangulating the registered data, yielding the one three-dimensional image of the oral cavity.

13. The three-dimensional digital image of a human oral cavity of claim 12, produced by the process wherein generating shape-from-shading data further comprises:
  estimating the direction of the illuminant from the plurality of two-dimensional images, in reference to camera intrinsic parameters.

14. A system for dental diagnosis comprising:
  a processor; and
  software means operative on the processor for generating a three-dimensional image of a human jaw using a plurality of two-dimensional images of the human jaw, including generating shape-from-shading data that is generated from a direction of an illuminant of the jaw that is estimated in reference to camera intrinsic parameters and from a determination of a solution to a brightness equation to yield the shape-from shading data that comprises a plurality of three-dimensional points.

15. A computerized method for dental imaging comprising:
  receiving a plurality of two-dimensional images of a oral cavity;
  generating shape-from-shading data from the plurality of two-dimensional images using a shape-from-shading process, the shape-from-shading data comprising a first plurality of three-dimensional points;
  generating range data comprising a second plurality of three-dimensional points from the plurality of two-dimensional images using a range-data process;
  fusing the range data to the shape-from-shading data, yielding fused data comprising a third plurality of three-dimensional points;
  registering the fused data, yielding registered data comprising a fourth plurality of three-dimensional points; and
  triangulating the registered data, yielding at least one three-dimensional image of the oral cavity.

16. The computerized method of claim 15, wherein the generating shape-from-shading data further comprises:

estimating the direction of the illuminant from the plurality of two-dimensional images, in reference to camera intrinsic parameters; and determining a solution to a brightness equation, yielding the shape-from-shading data comprising a first plurality of three-dimensional points.

17. The computerized method of claim 15, wherein the fusing the range data to the shape-from-shading data further comprises:

calculating an error difference in available depth measurements of the range data and the shape-from-shading data;

approximating a surface that fits the error difference, yielding an approximated surface; and correcting the shape-from-shading data from the approximated surface, yielding fused data comprising a third plurality of three-dimensional points.

18. A computer-readable medium having computer-executable instructions to cause a computer to perform a method comprising:

receiving a plurality of two-dimensional optical images of an oral cavity; and generating shape-from-shading data from the plurality of two-dimensional images using a shape-from-shading process, the shape-from-shading data comprising a first plurality of three-dimensional points;

generating range data comprising a second plurality of three-dimensional points from the plurality of two-dimensional images using a range-data process;

fusing the range data to the shape-from-shading data, yielding fused data comprising a third plurality of three-dimensional points;

registering the fused data, yielding registered data comprising a fourth plurality of three-dimensional points; and triangulating the registered data, yielding at least one three-dimensional image of the oral cavity.

19. The computerized method of claim 18, wherein the generating shape-from-shading data further comprises:

estimating the direction of the illuminant from the plurality of two-dimensional images, in reference to camera intrinsic parameters; and determining a solution to a brightness equation, yielding the shape-from-shading data comprising a first plurality of three-dimensional points.

20. The computerized method of claim 18, wherein the fusing the range data to the shape-from-shading data further comprises:

calculating an error difference in available depth measurements of the range data and the shape-from-shading data;

approximating a surface that fits the error difference, yielding an approximated surface; and correcting the shape-from-shading data from the approximated surface, yielding fused data comprising a third plurality of three-dimensional points.

21. A computerized method for dental imaging comprising:

receiving a plurality of two-dimensional images of a oral cavity; and generating at least one three-dimensional image of the oral cavity from the plurality of two-dimensional images, including:

generating shape-from-shading (SFS) data and range data using the plurality of two-dimensional images;

fusing the range data to the shape-from-shading data, yielding fused data comprising a third plurality of three-dimensional points;

registering the fused data, yielding registered data comprising a fourth plurality of three-dimensional points; and triangulating the registered data, yielding the at least one three-dimensional image of the oral cavity model.

22. The computerized method of claim 21, wherein the generating shape-from-shading data further comprises:

estimating the direction of the illuminant from the plurality of two-dimensional images, in reference to camera intrinsic parameters; and determining a solution to a brightness equation, yielding the shape-from-shading data comprising a first plurality of three-dimensional points.

23. The computerized method of claim 21, wherein the fusing the range data to the shape-from-shading data further comprises:

calculating an error difference in available depth measurements of the range data and the shape-from-shading data;

approximating a surface that fits the error difference, yielding an approximated surface; and correcting the shape-from-shading data from the approximated surface, yielding fused data comprising a third plurality of three-dimensional points.

24. A computer-readable medium having computer-executable instructions to cause a computer to perform a method comprising:

receiving a plurality of two-dimensional optical images of an oral cavity; and generating at least one three-dimensional image of the oral cavity from the plurality of two-dimensional images, including:

generating shape-from-shading (SFS) data using the plurality of two-dimensional images;

generating range data using a digitizer arm;

fusing the range data to the shape-from-shading data, yielding fused data comprising a third plurality of three-dimensional points;

registering the fused data, yielding registered data comprising a fourth plurality of three-dimensional points; and triangulating the registered data, yielding the at least one three-dimensional image of the oral cavity.

25. The computerized method of claim 24, wherein the generating shape-from-shading data further comprises:

estimating the direction of the illuminant from the plurality of two-dimensional images, in reference to camera intrinsic parameters; and determining a solution to a brightness equation, yielding the shape-from-shading data comprising a first plurality of three-dimensional points.

26. The computerized method of claim 24, wherein the fusing the range data to the shape-from-shading data further comprises:

calculating an error difference in available depth measurements of the range data and the shape-from-shading data;

approximating a surface that fits the error difference, yielding an approximated surface; and correcting the shape-from-shading data from the approximated surface, yielding fused data comprising a third plurality of three-dimensional points.

27. A computerized system comprising:

a digitizer providing five degrees of freedom, having an arm;

a charge coupled device camera, rigidly mounted on the arm of the digitizer; and a computer, operably coupled to the digitizer and the camera, receiving coordinate measurements from the digitizer and a plurality of two-dimensional images from the camera and generating a digital three-dimensional model from the coordinate measurements and from the plurality of two-dimensional images, the computer further including a computer-readable medium comprising means of:

generating shape-from-shading data from the plurality of two-dimensional images using a shape-from-shading process, the shape-from-shading data comprising a first plurality of three-dimensional points;

generating range data comprising a second plurality of three-dimensional points from the plurality of two-dimensional images using a range-data process;

fusing the range data to the shape-from-shading data, yielding fused data comprising a third plurality of three-dimensional points;

registering the fused data, yielding registered data comprising a fourth plurality of three-dimensional points; and triangulating the registered data, yielding the image of the digital three-dimensional model.

28. The computerized system of claim 27, further comprising:

a rapid prototyping machine operably coupled to the computer to receive the digital three-dimensional model and to generate a physical model of the digital three-dimensional model.

29. The computerized system of claim 27, further comprising:

a display operably coupled to the computer to receive the digital three-dimensional model and to generate an image of the digital three-dimensional model.

* * * * *

UNITED STATES PATENT AND TRADEMARK OFFICE
CERTIFICATE OF CORRECTION

| | | |
|---|---|---|
| PATENT NO. | : 7,084,868 B2 | Page 1 of 1 |
| APPLICATION NO. | : 09/842587 | |
| DATED | : August 1, 2006 | |
| INVENTOR(S) | : Aly A. Farag, David Tasman and Sameh M. Yamany | |

It is certified that error appears in the above-identified patent and that said Letters Patent is hereby corrected as shown below:

Column 14, line 42, in Claim 1, delete "distribution" and insert --digitizing--, therefor.

Column 14, line 46, in Claim 1, delete "that" and insert --the--, therefor.

Column 15, line 31, in Claim 7, delete "generating and range" and insert --generating range--, therfor.

Column 18, line 9, in Claim 21, delete "model".

Signed and Sealed this

Thirty-first Day of October, 2006

JON W. DUDAS
*Director of the United States Patent and Trademark Office*